US005582982A

United States Patent [19]
Cubbage et al.

[11] Patent Number: 5,582,982
[45] Date of Patent: Dec. 10, 1996

[54] BACKGROUND-REDUCING COMPOUNDS FOR PROBE-MEDIATED FLUORIMETRIC FLOW CYTOMETRIC ASSAYS

[75] Inventors: Michael L. Cubbage, Houston; Shyh C. Ju, Flowermound; Nagindra Prashad, Houston; William D. Weber; Joel Bresser, both of Bellaire, all of Tex.

[73] Assignee: Aprogenex, Inc., Houston, Tex.

[21] Appl. No.: 243,597

[22] Filed: May 16, 1994

Related U.S. Application Data

[63] Continuation-in-part of Ser. No. 915,894, Jul. 17, 1992, abandoned.
[51] Int. Cl.$^6$ ............................... C12Q 1/70; C12Q 1/68; G01N 33/53
[52] U.S. Cl. ..................... 435/6; 435/5; 435/7.1
[58] Field of Search ....................... 435/6, 5, 7.1

[56] References Cited

U.S. PATENT DOCUMENTS

| | | | |
|---|---|---|---|
| 4,192,917 | 3/1980 | Zurawski | 435/236 |
| 4,658,020 | 4/1987 | Kung et al. | 530/387 |
| 4,770,992 | 9/1988 | Van Den Engh et al. | 435/6 |
| 4,800,159 | 1/1989 | Mullis et al. | 435/172.3 |
| 4,863,875 | 9/1989 | Bailey et al. | 436/518 |
| 4,968,601 | 11/1990 | Jacobson et al. | 435/5 |
| 4,994,373 | 2/1991 | Stavrianopoulos et al. | 435/6 |
| 5,032,381 | 7/1991 | Bronstein et al. | 424/9 |
| 5,073,497 | 12/1991 | Schwartz et al. | 436/8 |
| 5,106,730 | 4/1992 | Van Ness et al. | 435/6 |
| 5,118,602 | 6/1992 | Pedersen et al. | 435/5 |
| 5,130,238 | 7/1992 | Malek et al. | 435/91 |
| 5,177,073 | 1/1993 | Gulliya et al. | 514/224.8 |
| 5,215,971 | 1/1993 | Datema et al. | 514/49 |

FOREIGN PATENT DOCUMENTS

| | | | |
|---|---|---|---|
| 9010715 | 9/1990 | WIPO | C12Q 1/68 |

OTHER PUBLICATIONS

Lundemose et al. "Detection of Chlamydia in Postmortal Formalin–Fixed Tissue" 1989, APMIS 97:68–74.
Spadoro et al. "Single Copies of HIV Proviral DNA Detected by Fluorescent In–Situ Hybridization", 1990, Biotechniques 8:186–193.
Schloter et al. "Sensitive Chemoluminescence–Based Immunological Quantification of Bacteria in Soil Extracts With Monoclonal Antibodies", 1992 May, Soil Biol. Biochem. 24:399–403.
Carmagnola et al "The Idiotypic Specificities of Lymphocytes in Human Monoclonal Analysis With the Fluorescence Activated Cell Sorter", 1983, Clin. Exp. Immunol. 51:173–177.
Bourinbaiar, et al. "Microwave Irradiation–Accelerated In Situ Hybridization Technique for HIV Detection", 1991, J. Virol. Methods 35:49–58.
Lawrence et al. "Subcellular Localization of Low Abundance Human Immunodeficiency Virus Nucleic Acid Sequences Visualized by Fluorescence In Situ Hybridization". 1990, PNAS 87:5420–5424.
Birkelund et al "Characterization of Native and Recombinant 75 Kilodalton Immunogens From *Chlamydia Trachomatis* Serovar L2". Infect. Immun. 1989, 57:2683–2690.
Lynch et al. "Application of a Modified Indirect Fluorescent Antibody Test to the Detection of Antibodies to Bovine Respiratory Syncytial Virus in Ontario Cattle", 1986. Can. J. Vet. Res. 50:384–389.
Stratagene Catalog, (1988) p. 39.
Lin et al., Issued 1990, Arteriosclerosis, "Role of Dying Endothelial Cells in Transendothelial Macromolecular Transport," vol. 10, pp. 703–709.
Louis et al., Issued 1989, Neuroscience Letters,"Antibodies to calcitonin–gene related peptide reduce inflammation induced by topical mustard oil but not that due to carrageenin in the rat," pp. 257–260.
Moreira et al., Issued 1989, Virchows Archiv A *Pathological Anatomy and Histopathology*, "A procedure to obtain long-lasting fluorescence in formaldehyde fixed tissues.", vol. 415, pp. 391–393.
Schols et al., Issued 1989, Journal of Acquired Immune Deficiency Syndromes, "Flow Cytometric Method to demonstrate Whether Anti–HIV–1 Agents Inhibit Virion Binding to T4$^+$ Cells," vol. 2, pp. 10–15.
Schols et al., Issued 1989, J. Gen. Virol., "Syncytium Formation and Destruction of Bystander CD4$^+$ Cells Cocultured with T Cells Persistently Infected with Human Immunodeficiency Virus as Demonstrated by Flow Cytometry," vol. 70, pp. 2397–2408.
Blach et al., Issued 1988, Gamete Research, "Use of a Monoclonal Antibody to Evaluate Integrity of the Plasma Membrane of Stallion Sperm," vol. 21, pp. 233–241.
Benjouad et al. Issued Mar. 1993, Federation of European Biochemical Societies, "Cytotokic Effect on Lymphocytes of Tat From Human Immunodeficiency Virus (HIV–1)" pp. 119–124, vol. 319.
Kan et al., Issued 1991, Experimental Gerentology, "Effect of Vitamin E on the Accumulation of Fluorescent Material in Cultured Cereberal Cortical Cells of Mice", vol. 26, pp. 365–374.
Yourno et al., "A Novel Polymerase Chain Reaction Method for Detection of Human Immunodeficiency Virus in Dried Blood Spots on Filter Paper," Journal of Clinical Microbiology, issued 1992, vol. 30, pp. 2887–2892.

*Primary Examiner*—W. Gary Jones
*Assistant Examiner*—Jeffrey Fredman
*Attorney, Agent, or Firm*—Elman & Associates

[57] ABSTRACT

Assays for target molecules in biological cells whereby the use of appropriate light absorbing molecules at an appropriate stage of the assay procedure leads to decreased non-specific emission of light and/or decreased autofluorescence.

19 Claims, 6 Drawing Sheets

BACKGROUND-REDUCING COMPOUNDS FOR PROBE-MEDIATED FLUORIMETRIC FLOW CYTOMETRIC ASSAYS

This application is a continuation-in-part of application Ser. No. 07/915,894 filed Jul. 17, 1992, now abandoned, which application is hereby incorporated by reference.

FIELD OF THE INVENTION

This invention pertains to the reduction of background fluorescence in fluorimetrically-monitored assays for specific molecules in biological cells and viruses.

BACKGROUND OF THE INVENTION

In an important type of in situ assay, a cell is incubated with a target-specific probe that is attached to a fluorescent dye and subsequently the probe molecules that have bound to the target are detected fluorimetrically. Detection is normally accomplished with a flow cytometer or microscope. Such assays are useful to detect viral nucleic acids, human genes of interest, and specific cellular or viral antigens.

In the first steps of a typical fluorimetric measurement, a cell is exposed to light with a wavelength that the probe dye can absorb. The dye will then emit the light at a longer wavelength. A significant problem, however, is that the light emitted by a probe-treated cell will not exclusively originate from fluorescent probe molecules bound to specific target molecules. Rather some of the light emitted will be from probe molecules that have bound non-specifically; additionally, light will be emitted by cellular molecules.

If the probe molecule has a nucleic acid moiety, probe specificity derives from the fact that a target nucleic acid in the cell has a base sequence that is complementary to that of the probe. Where such complementarity exists, and under conditions where the probe can diffuse into the proximity of the target nucleic acid, the probe and target nucleic acids enter into a double-stranded hybrid molecule relatively efficiently. Independent of such specific reactions, however, the probe molecule will, to some extent, bind to nucleic acid molecules that are not perfectly complementary to the probe, to protein molecules, and to other non-nucleic acid molecules in the cell. Such binding is referred to collectively as non-specific background binding and the light emitted by probes involved in such binding is non-specific background emission.

If the probe has an antibody moiety, specificity derives from the fact that the antibody will react with a specific antigen. Non-specific binding can also occur, however.

In addition to the fluorescent probes in the cell, however, there are cellular molecules which have the capacity to absorb and emit light. Such emitted light is referred to as autofluorescence, and the molecules which produce it are autofluorescing molecules.

The present invention involves the discovery of compounds useful as background reducers in fluorimetric in situ assays.

In addition to the general benefit of increased assay sensitivity that the background reducers provide, there is the additional advantage that, for a given level of sensitivity to be reached, cell treatment procedures such as cell fixation need not be as detrimental to cell integrity as would be the case without the use of the background reducers. As a result, the cells retain their structural integrity for a longer time, as a consideration particularly important for flow cytometry.

BRIEF SUMMARY OF THE INVENTION

The present inventions are processes whereby the use of appropriate light absorbing molecules at an appropriate stage of the assay procedure leads to decreased non-specific emission of light and/or decreased autofluorescence.

THE PRIOR ART

Prior attempts to reduce non-specific background binding have focused on the use of large amounts of molecules similar in structure to the probe molecules (e.g. salmon sperm DNA for use with nucleic acid probes, albumin for use with antibody probes). Such background-reducing molecules were not labeled with a fluorescent dye and were apparently added on the theory that they will compete for the same non-specific sites as the probe does.

Evans Blue, one of the background-reducing compounds used in the present invention has been previously used by others as a counterstain, but not in a fluorescent in situ assay.

DETAILED DESCRIPTION

In a general aspect, the invention is an analytical process whereby the number of probe molecules bound to a biological entity (i.e., a cell or virus) is used as a measure of the amount of target molecules in that entity. The process comprises the steps of:

(1) incubating a biological entity with a fluorescent probe in solution;

(2) removing the biological entity from that solution, (3) exposing the biological entity to light at absorption wavelengths of the fluorescent probe, and (4) measuring the amount of light emitted at emission wavelengths of the fluorescent probe;

wherein at a time after the commencement of step (1) and prior to the termination of step (4), a background-reducing compound is present in the solution within which the biological entity is suspended;

said background-reducing compound comprising a light absorbing moiety with a structure different than that of the fluorescent dye moiety of the fluorescent probe;

said background-reducing compound having an absorption wavelength range (the range of wavelengths over which it absorbs light when the process is performed) that includes of the emission wavelengths of the fluorescent probe (the range of wavelengths over which light is emitted by the probe) at which the amount of light is measured in step (4).

For a light-absorbing compound to be an effective background reducer with regard to a range of wavelengths, it is preferred that it have an average molar extinction coefficient in that range that is at least 2 percent as great as the average molar extinction coefficient of Trypan Blue in the range 520 nm to 560 nm; it is more preferred that it have a molar extinction coefficient in that range that is at least 10 percent as great as the average molar extinction coefficient of Trypan Blue in the range 520 nm to 560 nm.

Because many cytofluorimetric measurements are made in the visible range, about 400 nm to 660 nm, background reducers that are effective in that range are particularly valuable. There is no need, however, for a cytofluorimetric measurement to be done in the visible range; therefore, background reducers that absorb somewhere in the range 250 to 1000 nm, can also be useful in particular situations. Indeed, the principle of the invention is applicable to any wavelength at which a cytofluorimeter can be used.

"Light" in the present context refers to light that is detected by a flow cytometer or an observer or camera using a fluorescent microscope. As such, light will normally be light in the visible range, but if for particular purposes the cytometer or microscope is altered to detect photons with energies greater or lower than that of visible light, then such photons are also considered to fall within the term "light" for present purposes.

The light absorbing moiety of the background-reducing compound, because it has a different structure than the fluorescent dye moiety of the fluorescent probe, will normally have the desirable property that, if it emits light at all (i.e., it is a fluorescent compound), will have an emission spectrum different from that of the fluorescent moiety (i.e., as regards a given amount of light of a given wavelength that has been absorbed, there will be differences in the intensity of light emitted as a function of wavelength).

As a result of its presence in the solution containing the cell, the background-reducing compound will diffuse onto and into the biological entity. Therefore, if the background-reducing compound is added to a solution prior to steps (3) and (4), and is not in the solution used for steps (3) and (4), there will be residual amounts of the background-reducing compound in or on the entity during steps (3) and (4) and some beneficial effect will be obtained. Nevertheless, it is preferable that the background-reducing compound be in the solution in which the entity are suspended in steps (3) and (4).

As will be evident from the Examples, the analytical process is normally applied substantially simultaneously to a large number of cells or viruses.

Frequently, the amount of light emitted will be used as the basis for determining whether target molecules are present in a cell. If the amount of light emitted exceeds a certain specified amount, the cell is considered to have target molecules.

It is hypothesized that the invention is effective partly because the background-reducing compound binds to at least some of the same non-specific targets as the probe does and, because the background-reducing compound and the probe are in close proximity, the background-reducing compound will absorb emissions from the probe. Additionally, the background-reducing compound will absorb light emitted due to autofluorescence by non-probe molecules in the biological entity. After absorbing light emitted by either nonspecifically bound probe or autofluorescing molecules, the background compound may emit light at its own emission wavelengths. As will be seen from the Examples below, the light emitted by the specifically bound probe molecules is absorbed to a lesser extent by the back-reducing compounds; therefore, the overall sensitivity of the analytical process is improved.

In a preferred embodiment of the process, steps (3) and (4) both take place while the cell or virus is still resuspended in the probe-free solution containing the background reducing compound. Regardless of whether the preferred process or an alternative is chosen, the cells or viruses should remain in the probe-free solution comprising the background-reducing compound for a time great enough to allow them to absorb the background-reducing compound. Five minutes is a convenient time for that purpose, but there is wide latitude as to what length of time is used.

It is preferred that fluorescence measured within 45 min of addition of background reducer; however, if the background reducer is in the solution used for steps (3) and (4), one can wait up to 24 hours to do fluorescent measurement.

In a particularly preferred embodiment of the process, the process further comprises a wash step between the steps numbered (2) and (3) above. A wash step can be performed by centrifuging the cells or viruses out of the solution in which they are suspended, then suspending them in a wash solution, and then centrifuging the cells or viruses out of the wash solution. A wash solution is generally a probe-free solution, it may or may not have the background reducing compound suspended in it.

The probe will comprise a fluorescent dye. It can also comprise, covalently attached to the dye, either a single-stranded nucleic acid (DNA or RNA) moiety or an antibody moiety. A moiety is part of a molecule. For example, the portion of a probe that has been contributed by a nucleic acid is a nucleic acid moiety; the portion that has been contributed by the fluorescent dye is the fluorescent dye moiety. The covalent attachment may occur via a linker, where the dye and the nucleic acid molecule (or antibody) are linked at different sites to the linker molecule.

Nucleic acid probes can be used against a variety of nucleic acid targets, viral, prokaryotic, and eukaryotic. The target may be a DNA target such as a gene (e.g., oncogene), control element (e.g., promoter, repressor, or enhancer), or sequence coding for ribosomal RNA, transfer RNA, or RNase P. The target may be RNA such as mRNA, ribosomal RNA, RNase P, tRNA, a viral genome or complementary copy thereof. Additionally, the target may be a "nucleic acid amplification product," i.e., a nucleic acid molecule, either DNA or RNA, which is the result of introducing an enzyme or enzymes into the cell so that such enzymes will make an nucleic acid molecule complementary to one already present in the cell. For example, O. Bagasra et al, *The New England Journal of Medicine,* 326, pp. 1385–1391 (1992), have disclosed the use of the polymerase chain reaction (PCR) with intact cells such that the introduction of polymerase molecules into a cell resulted in additional nucleic acid molecules being formed, each a copy of one previously existing in the cell, though not necessarily existing before the introduction of the enzymes.

A viral nucleic acid target may be part of a virus, in which case the virus may or may not be inside a cell. Alternatively, a viral nucleic acid target may not be part of a virus, but may be inside a cell.

The processes of this invention can be done for targets in biological entities that are either in liquid suspension, on slides or other solid supports, or in tissue sections. Such hybridization procedures are well known in the art. They are, for example, described in more detail in PCT applications WO 90/02173 and WO 90/02204. In the case of hybridization on slides, one preferred mounting solution (the one that the cells are immersed in for performance of the fluorescent measurements) is one with a background reducer dissolved along with 0.1% 1,4 phenylenediamine antifade and 1 µg/ml Hoechst (dye#33258) in a solution of 50% glycerol and 50% PBS.

The target molecules can be in any biological cell. The cells can come from solid tissue (e.g., nerves, muscle, heart, skin, lungs, kidneys, pancreas, spleen, lymph nodes, testes, cervix, and brain) or cells present in membranes lining various tracts, conduits and cavities (such as the gastrointestinal tract, urinary tract, vas deferens, uterine cavity, uterine tube, vagina, respiratory tract, nasal cavity, oral cavity, pharynx, larynx, trachea, bronchi and lungs) or cells in an organism's fluids (e.g., urine, stomach fluid, sputum, blood and lymph fluid) or stool.

The cells containing the target molecules may be eukaryotic cells (e.g., human cells), prokaryotic cells (e.g. bacteria), plant cells, or any other type of cell. They can be simple eukaryotes such as yeast or be derived from more complex eukaryotes such as humans.

The target molecules can be in a non-enveloped virus or an enveloped virus (having an enveloping membrane such as a lipid-protein membrane).

The hybridization assay may be done with fixed cells (or fixed viruses). Useful precipitation fixatives include ethanol, acetic acid, methanol, acetone and combinations thereof.

Fixatives and hybridization of fixed cells, in general, are discussed in PCT international applications, WO 90/02173 and WO 90/02204 of Research Development Corp. Fixatives that provide good preservation of cellular morphology and preservation and accessibility of antigens, and high hybridization efficiency.

The fixative may contain a compound which fixes the cellular components by cross-linking these materials together, for example, parafomaldehyde, glutaraldehyde or formaldehyde. Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

The hybridization solution may typically comprise a chaotropic denaturing agent, a buffer, a pore forming agent, a hybrid stabilizing agent.

The chaotropic denaturing agents (Robinson, D. W. and Grant, M. E. (1966) J. Biol. Chem. 241: 4030; Hamaguchi, K. and Geiduscheck, E. P. (1962) J. Am. Chem. Soc. 84: 1329) include formamide, urea, thiocyanate, guanidine, trichloroacetate, tetramethylamine, perchlorate, and sodium iodide. Any buffer which maintains pH at least between 7.0 and 8.0 may be utilized.

The pore forming agent is for instance, a detergent such as Brij 35, Brij 58, sodium dodecyl sulfate, CHAPS™ Triton X-100. Depending on the location of the target biopolymer, the pore-forming agent is chosen to facilitate probe entry through plasma, or nuclear membranes or cellular compartmental structures. For instance, 0.05% Brij 35 or 0.1% Triton X-100 will permit probe entry through the plasma membrane but not the nuclear membrane. Alternatively, sodium desoxycholate will allow probes to traverse the nuclear membrane. Thus, in order to restrict hybridization to the cytoplasmic biopolymer targets, nuclear membrane pore-forming agents are avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function.

Hybrid stabilizing agents such as salts of mono- and di-valent cations are included in the hybridization solution to promote formation of hydrogen bonds between complementary sequences of the probe and its target biopolymer. Preferably sodium chloride at a concentration from 0.15M to 1M is used. In order to prevent non-specific binding of nucleic acid probes, nucleic acids unrelated to the target biopolymers are added to the hybridization solution.

Many types of solid supports may be utilized to practice the invention. Supports which may be utilized include, but are not limited to, glass, Scotch tape (3M), nylon, Gene Screen Plus (New England Nuclear) and nitrocellulose. Most preferably glass microscope slides are used. The use of these supports and the procedures for depositing specimens thereon will be obvious to those of skill in the art. The choice of support material will depend upon the procedure for visualization of cells or viruses and the quantitation procedure used. Some filter materials are not uniformly thick and, thus, shrinking and swelling during in situ hybridization procedures is not uniform. In addition, some supports which auto fluoresce will interfere with the determination of low level fluorescence. Glass microscope slides are most preferable as a solid support since they have high signal-to-noise ratios and can be treated to better retain tissue.

In a particular embodiment of the process, the cell is a human cell and the probe is specific for the nucleic acid of a virus (viral nucleic acid), especially one considered pathogenic for humans. Viral nucleic acid, either RNA or DNA, is acid that has the same nucleotide sequence as the genetic material of the virus or a nucleotide sequence complementary to that of the genetic material. In another, particular embodiment of the process, the probe is specific for a human gene of interest or an RNA transcript of such a gene.

The term "staining dye" is used here for dyes that are incubated with the cell after the hybridization step has been completed. ("Probe dyes" are part of probes and are incubated with the cells during the hybridization step.) Some staining dyes are effective background reducers; many are also effective as counterstains.

Emission and absorption maximum wavelength data have been published for many dyes and other light absorbing compounds (see, for example, the Merck Index or the catalog of Aldrich Chemical Company, Milwaukee, Wis.). Such data is suggestive of which compounds can be useful, but not definitive. A scanning fluorimeter will give an entire emission or absorption spectrum. Some background-reducing compounds are listed below for some probe dyes. The efficacy of a background-reducing compound as regards a given probe dye can, however, be tested relatively easily using the procedures set forth in the Examples below.

Fluorescein, which is frequently used as a fluorescent probe dye, has a maximum absorption wavelength at approximately 488 nm and maximum emission wavelength at approximately 525 nm.

Light-absorbing compounds that are good background reducers include azo dye derivatives that have a polyaromatic conjugate moiety and, on that moiety, have one or more polar groups such as a nitro group ($-NO_2$), a sulfonyl group ($-SO_3$), or an amino group ($-NH_2$). They are probably good because they tend to bind to the same proteins and membranes as the non-specifically bound probes.

A few of the many probe dyes for which this invention is useful are flourescein, FITC, Texas Red, Coumarin, Rhodamine, Phycoerythrin, and Perci-P.

Some background-reducing compounds for use with the probe dye, fluorescein (or fluorescein isothiocyanate (FITC)) are Azocarmine B, Acid Red 114, Evans Blue, Palatine Fast Black Wan, Trypan Blue, Naphthol Blue Black and Sulforhodamine 101.

Some background-reducing compounds for use with the probe dye, Texas Red are Naphthol Blue Black and Palatine Fast Black WAN.

For probe dyes other than fluorescein, the background reducing compounds of value might differ from those used with fluorescein- or FITC-labeled probes. It is preferred that, in the emission wavelength range of the probe dye that will be detected by the fluorimeter, fluorescent microscope or flow cytometer, the background reducing compound have an average molar extinction coefficient at least two percent (more preferably 10 per cent) that of Trypan Blue in the range 520 nm to 560 nm.

For any dye fluorescent probe, there are many compounds that will act as a background reducer.

The inventions are also kits useful for carrying out the inventions. Such a kit would comprise a fluorescent-labeled probe and a background reducing compound appropriate for use with such a probe in carrying out the process inventions set forth here.

Dye Abbreviations Used

TABLE 1

Dye abbreviations used here

| Dye Number | Actual Dye Name | Abbreviation |
|---|---|---|
| 12 | Naphthol Blue Black | Naphthol Bl. Blk. |
| 13 | Palatine Fast Black WAN | Palatine F-B WAN |
| 20 | Sulforhodamine 101 hydrate | Sulforhodamine 101 |
|  | Fluorescein isothiocyanate | FITC |

Probes Used in the Examples

The HIV probe was a mixture of non-overlapping DNA 25-mers covering the regions 126–3375, 4401–5150, 5176–5400, 5426–5650, 5676–7775, and 8150–8500, as specified under the locus name HIVBH102 in Gen Bank™ Release 65.0. A "25-mer" is an oligonucleotide containing 25 bases.

The NR probe was a DNA 25-mer that binds to part of the bacterial nitrogen reductase gene; its nucleic acid moiety has the sequence, TACGCTCGATCCAGCTATCAGCCGT (SEQ ID NO: 1). (For all sequences described, the 5' end is at the left end.)

The 28s RNA probe was a DNA 25-mer that binds to 28s ribosomal RNA; its nucleic acid moiety has the sequence, ATCAGAGTAGTGGTATFTCACCGGC (SEQ ID NO: 2).

The probes were synthesized (Applied Biosystems DNA Synthesizer Model 380 B using the recommended A.B.I. reagents) and in the last stage an aminohexyl linker was attached to the 5' end phosphate. The 5' aminohexyl oligodeoxynucleotides were then coupled to a FITC dye molecule (from Molecular Probes) and purified by HPLC.

Flow Cytometry Performed for the Examples

A Coulter Profile II flow cytometer was used. For experiments with fluorescein as the probe dye, the filter for FL3 was a 635 long pass filter; i.e., it allows any light over 635 nm wavelength to pass. For FL1, a 540 bp (40) filter was used; i.e., only light with a wavelength between 520 nm and 560 nm is allowed to pass. The excitation wavelength was 488 nm.

PMT1 and PMT3 settings were adjusted as convenient for each experiment. A typical useful combination is a PMT1 setting of 1100 and a PMT3 setting of 900, with a color compensation, PMT1–PMT3, of 15%.

Solutions Used in the Examples

The following solutions were those used in the Examples. It will be clear to a person of ordinary skill in the art that the composition of the solutions can be varied to some extent without deviating from the spirit and scope of the invention.

Fixation solution F had the following ingredients: 4 volumes ethanol, 5 volumes of 1×PBS, and 1 volume of glacial acetic acid.

Hybridization cocktail HC had the following ingredients: 5×SSC; 30% Formamide (v/v); 3% Triton X-100 (v/v); 0.4M Guanidinium isothiocyanate; 0.16M sodium phosphate buffer (pH 6); 15×Ficoll/PVP; 1 mg/ml sheared salmon sperm DNA; 10 mM EDTA; 25 mM DTT; 5% PEG 4000; 10 ug/ml (microgram/ml) probe. In the foregoing, 500×PVP is 5 g of Ficoll type 400 (polysucrose 400,000 mol. wt.) plus 5 g of PVP (polyvinylpyrrolidinone) dissolved in water to a total volume of 100 ml; 15×Ficoll/PVP indicates that 500×Ficoll/PVP is diluted with water by a factor of 15/500.

Wash solution #1 had the following composition: 0.4M guanidinium isothiocyanate; 0.1% Triton X-100 (an alcohol derivative of polyoxyethylene ether, see Aldrich Chemical Co. catalogue for 1990–91; v/v); 0.1×SSC; in deionized water.

Wash solution #2 had the following composition: 0.1% Triton X-100 (v/v); 0.1×SSC; in deionized water.

The staining dye solution had the following composition: 0.002% staining dye (w/v) in 1×PBS (phosphate buffered saline; 0.136M NaCl, 0.003M KCl, 0.008M $Na_2HPO_4.7H_2O$, 0.001M $KH_2PO_4$). Generally, the staining dye, if useful as and used as a background-reducer, can be present at a concentration between 0.0002% and 0.10% (w/v). The cells are preferably incubated with the background reducing compound between 20° C. and 46° and from 2 min up to 8 hours. Some staining dyes are also background-reducing compounds. Most also functioned as a counterstain.

The staining dye solution had the same composition as the flow buffer for the FAScan.

1×SSC had the following composition: 0.15M NaCl, 0.15M sodium citrate, pH 7.0. 2×SSC was composed so that upon a 1:1 dilution with water, SSC would be produced; 10×SSC was composed so that upon a 1:10 dilution with water, SSC would be produced.

Additional Useful Reagents and Solutions

Useful reagents and solutions for executing the inventions described herein include 10% dodecyl alcohol in the solution analyzed cytofluorimetrically; 5% (v/v) Vitamin E in the hybridization cocktail used where the assay target is in a biological entity; about 8% DMSO (v/v) with about 5% or 10% squalane and about 5% or 10% pyrrolidinone in the hybridization cocktail when the target is in a biological entity; 5 µl of 1M (1 molar) DTT and 5 µl of Proteinase K (1 mg/ml) solution are added to 100 µl of cocktail and the hybridization reactin is run, for example, at 42° C. for 5 min, then at 95° C. for 5 min, and then at 42° C. for 2 min, when the target is in a biological entity; and/or about 0.05% or 0.10% aurintricarboxylic acid (or 1–10 mg/ml basic fuchsin) in the hydbridization cocktail when the target is a biological entity and a fluorescent probe, especially one with a fluorescein or rhodamine derivative as a reporter group, is used.

Probes, where the target is in a biological entity can be made as phosphorothioate oligonucleotides, each 30-mer having four sulfur atoms, using an Applied Biosystem (ABI) DNA Synthesizer, Model 380B and the recommended ABI reagents. The sulfur atoms may be located as follows, one is at the extreme 5' end of the probe, a second is between the 7th and 8th nucleosides (counting from the 5' end), the third is between the 22nd and 23rd nucleosides, and the fourth is between the 29th and 30th nucleosides. The sulfur atoms of the polysulfurized oligonucleotides can then coupled to a fluorescent dye, iodoacetamido-fluorescein, as follows (smaller amounts can be synthesized by adjusting the volumes): 200 µg of dried oligonucleotide is dissolved in 100 µl of 250 mM Tris buffer, pH 7.4 to form a first solution. Then one mg of iodoacetamido-fluorescein is combined with 100 µl of dry dimethylformamide (i.e., 100 percent DMF) in a second solution. The two solutions are mixed together and shaken overnight. After the overnight incubation, the labeled oligonucleotide is precipitated with ethanol and 3M sodium acetate. This crude material is then loaded on to a PD-10 column to remove free dye. The desired fractions are then collected. The liquid phase is then removed under vacuum. The crude material is then purified with HPLC (high performance liquid chromatography).

Where 30-mers are used, probes against both strands of a double-stranded target can be used, provided that the probes are "out-of phase" along the map of the target so that any probe is not complementary in base sequence to more than about 15 nucleotides of a probe to the other strand of the target. In that way, probes hybridize to the target and not to each other.

If the probes are labelled at both their 3' and 5' ends with an aminohexyl linker, and tetramethylrhodamine is the dye attached to each linker, it is preferred to use 25-mers and space the targets along a given strand by five base pairs; and if both strands of a target are hybridized to, the end-over-end overlap of probes to opposite strands can be about 10 bases.

Cell Lines Used in the Examples

AcH2 cells are a human-derived lymphoma cell line.

H9 cells are a human-derived lymphoma cell line (ATCC No. CRL 8543).

Reagents

Reagents can be purchased from any of a variety of sources including Aldrich Chemical Co., Milwaukee, Wis., Sigma Chemical Co., St. Louis, Miss., Molecular Probes, Inc., Eugene, Oreg., Clontech, Palo Alto, Calif., Kodak, Rochester, N.Y., and SPectrum Chemical Manufacturing Corp., Gardenea, Calif.

EXAMPLE 1

Background-Reducing Compounds Used with Fluorescein-Labeled Probes

A purpose of this Example was to determine whether a compound functioned as a background reducer; i.e., whether it decreased the amount of light emitted by non-specifically bound probe molecules and autofluorescing molecules without causing a similar decrease in the amount of light emitted by specifically bound probe molecules.

As a test for non-specific binding, an "NR" probe was used. This oligonucleotide probe binds specifically to DNA sequences within the plant nitrogen reductase gene.

As a test for specific binding, a "28S" probe was used. This oligonucleotide probe binds specifically to the cell's ribosomal 28S RNA.

When the NR probe is used, the amount of light emitted will be the sum of the amount of light emitted by two sources: nonspecifically bound probe molecules and autofluorescing molecules. In other words, the amount of light emitted is background light.

When the 28S probe is used, the amount of light emitted is the sum of light emitted from three sources: specifically bound probe, nonspecifically bound probe and autofluorescing molecules. In other words, the amount of light emitted is target-specific light plus background light.

One seeks a compound that acts to reduce background light. Therefore one seeks a compound that maximizes the ratio, A/B, where A is the amount of light emitted when the 28S probe is used and B is the amount of light emitted when the NR probe is used. As a reference point, the ratio A/B is measured when no compound is added as a background reducer.

It is not sufficient, however, that the ratio A/B be maximized. Additionally, the amount of probe-specific light must be sufficiently high to be useful. The amount of probe specific light is (A–B). It can be seen that there is still an appreciable amount of probe specific light when the background reducing compound is used.

The experiments were conducted as follows:

1. Uninfected H9 cells were fixed in solution F, then resuspended in 2×SSC.

2. The cells were spun out of solution and resuspended in hybridization cocktail HC. The HC cocktail varied from sample to sample only as regards the probe used. Three types of probes were used: an NR probe, an HIV probe and a 28S RNA probe. Each probe had fluorescein linked to the probe's oligonucleotide.

3. After 30 min. at 42° C., the cells were washed in wash solution #1 preheated to 42° C. by centrifuging them out of the hybridization cocktail at 250×g for about 5 min.

4. Cells were next washed in wash solution #2 preheated to 42° C.

5. Cells were resuspended in a 1×PBS solution or PBS solution containing a compound to be tested for its effectiveness as a background reducer (that compound is also referred to in this Example as a staining dye).

6. Cells were run on a flow cytometer and histograms were generated which displayed the staining dye fluorescence in one axis (LFL2 or LFL3) and the probe fluorescence on the other axis (LFL1).

In step (6) a "Count vs. LFL1" histogram was generated. ("Count" refers to cell count.) This histogram was used as the basis for determining whether the compound tested was an effective background reducer. Additional histograms and an FS/SS plot were also generated but were not used as the basis for determining background reduction; they are not shown or summarized here.

Figure 1:
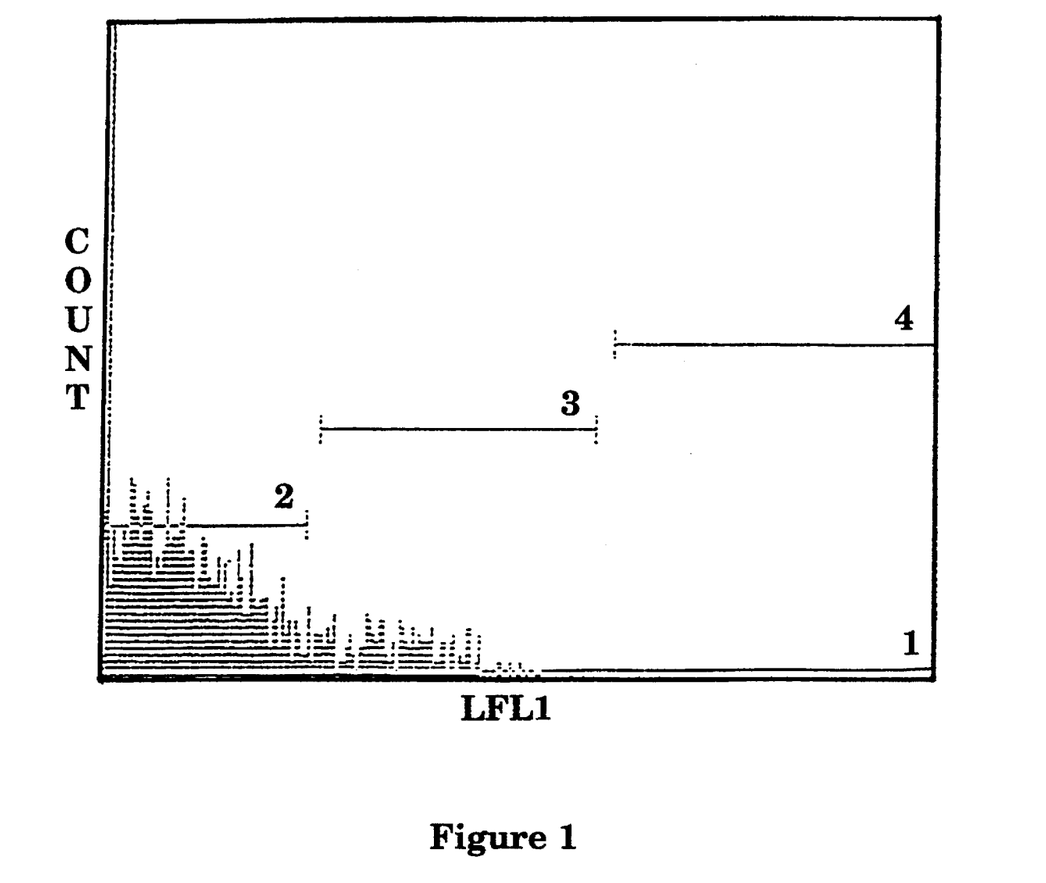
FIG. 1. "Count vs. LFL1" histograms, generated using sulforhodamine 101 hydrate as a background-reducing compound, of uninfected human H9 cells that had been incubated with a fluorescein-nucleic acid probe specific for the plant nitrogen reductase gene. (our sample #6112).
Figure 2:
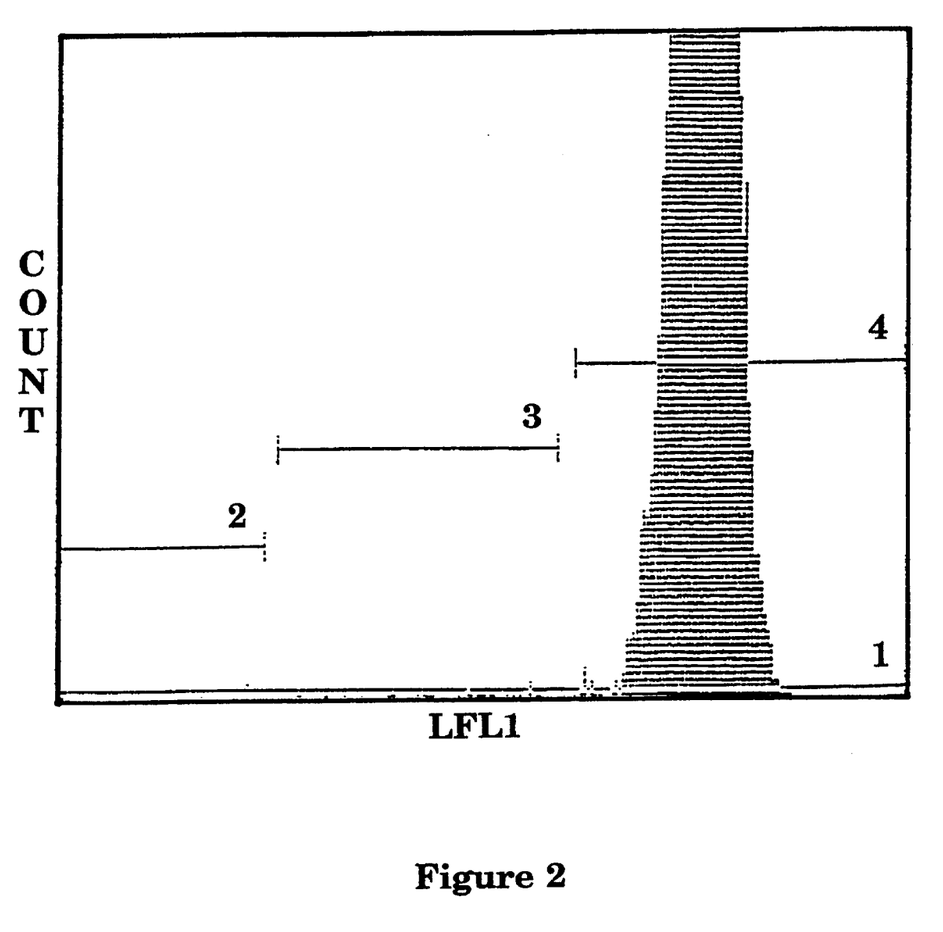
FIG. 2. "Count vs. LFL1" histograms, generated using sulforhodamine 101 hydrate as a background-reducing compound, of uninfected human H9 cells that had been incubated with a fluorescein-nucleic acid probe specific for 28S ribosomal RNA. (our sample #6114)

Examples of Count vs. LFL1 histograms that were generated using sulforhodamine 101 hydrate as a staining dye are shown in FIG. 1 (NR probe) and FIG. 2 (28S probe). Tables 2 and 3 summarize the results in these FIGS.

TABLE 2

Summary of results of Count vs. LFL1 histogram in FIG. 1

| Set | Cell Count | Cell Pct | Mean LFL1 |
|---|---|---|---|
| 1 | 4917 | 100.0 | 0.1560 |
| 2 | 4587 | 93.3 | 0.126 |
| 3 | 309 | 6.3 | 2.966 |
| 4 | 4 | 0.1 | 41.66 |

TABLE 3

Summary of results of Count vs. LFL1 histogram in FIG. 2

| Set | Cell Count | Cell Pct | Mean LFL1 |
| --- | --- | --- | --- |
| 1 | 5034 | 100.0 | 101.0 |
| 2 | 2 | 0 | 0.218 |
| 3 | 31 | 0.6 | 6.535 |
| 4 | 4999 | 99.3 | 103.0 |

In Tables 2 and 3, the columns "Pct Count" gives the percentage of the total cell count; "LFL" stands for "Log fluorescence".

The results for the staining dyes tested are summed up in the following table:

TABLE 4

Summary of results

| Dye No. | Staining dye | Mean for NR probe | Mean for HIV probe | Mean for 28S probe | Ratio of means 28S/NR ratio |
| --- | --- | --- | --- | --- | --- |
| 12 | Naphthol Bl. Blk. | 1.159 | 1.301 | 73.43 | 63.66 |
| 13 | Palatine F-B WA. | 0.726 | 1.030 | 63.76 | 87.82 |
| 14 | Trypan Blue | 0.266 | 0.259 | 77.56 | 291.6 |
| 20 | Sulforhodamine 101 | 0.156 | 0.143 | 101.0 | 647.4 |
| PBS | Phosph. Buffered Sal. | 64.5 | 38.73 | 246.1 | 3.82 |

"Ratio of means, 28S/NR" is the ratio of the mean for the NR probe to the mean for the 28S probe.

It can be seen from the right hand column in Table 4, which is a measure of the ratio A/B noted above, that all four staining dyes tested increased the ratio A/B. Furthermore the amount of probe specific light (A–B) was still substantial. Therefore all the staining dyes listed in Table 4 are useful as background reducers.

EXAMPLE 2

Use of Background Reducing Compound in Assay for HIV RNA in Hiv-Infected Cells

Figure 3:
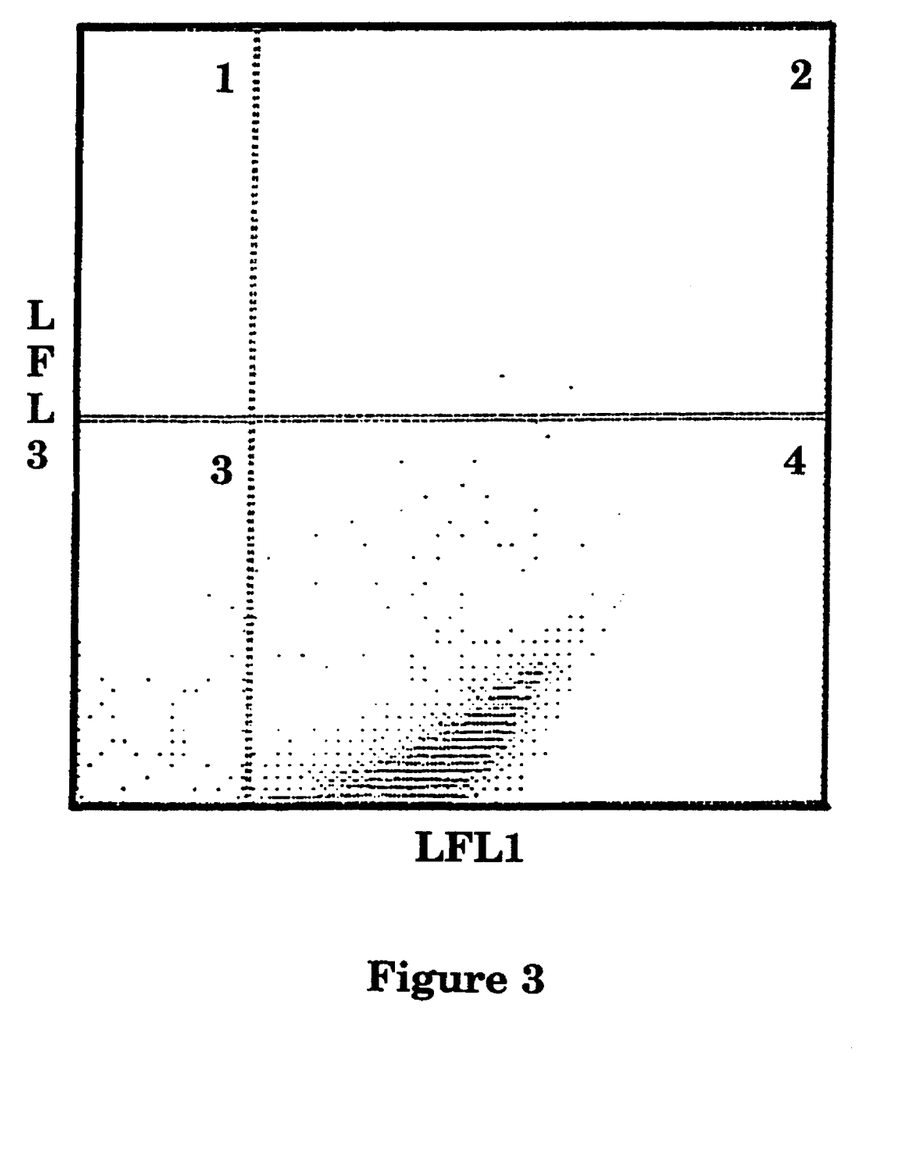
FIG. 3. LFL3 vs, LFL1 plot, HIV-infected cells; without a background-reducing compound. (our sample #2063)
Figure 4:
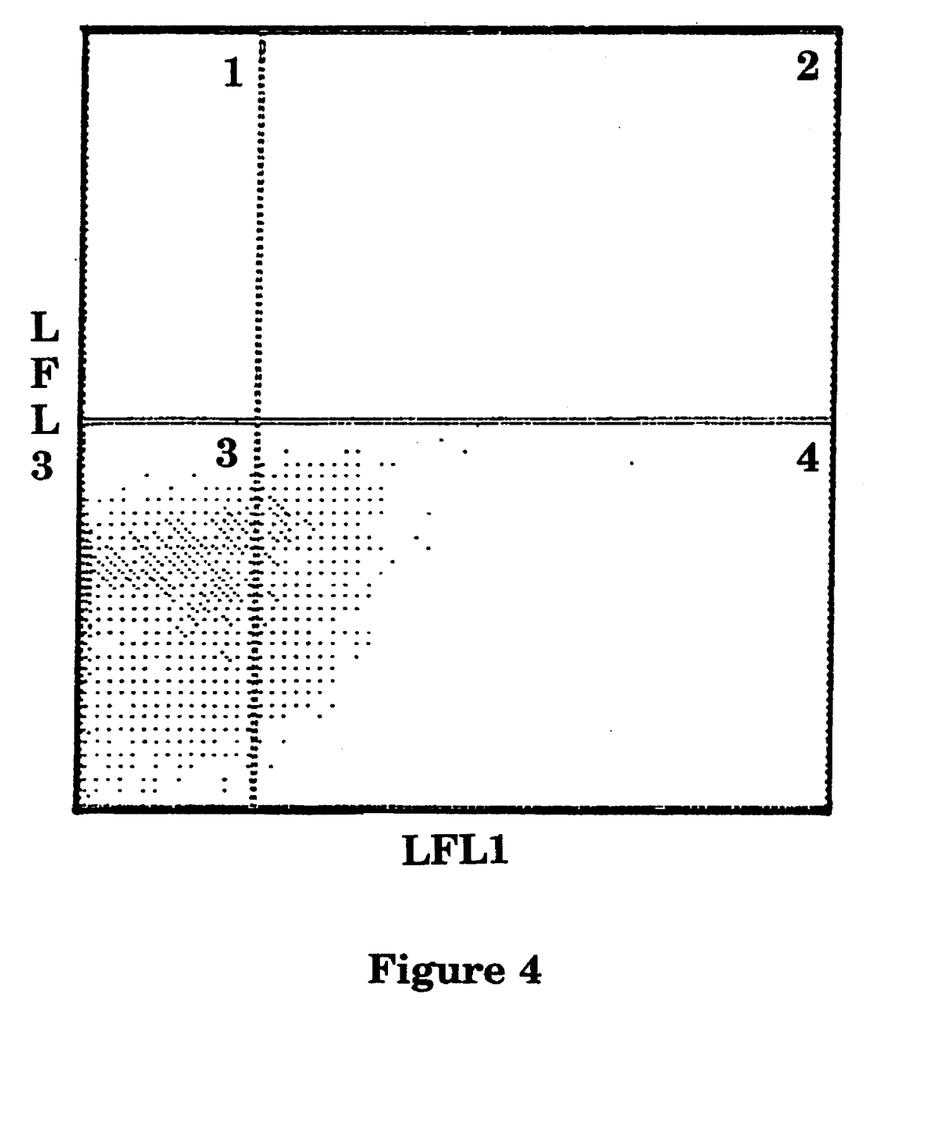
FIG. 4 LFL3 vs. LFL1 plot; uninfected cells; without a background-reducing compound. (our sample #2066)
Figure 5:
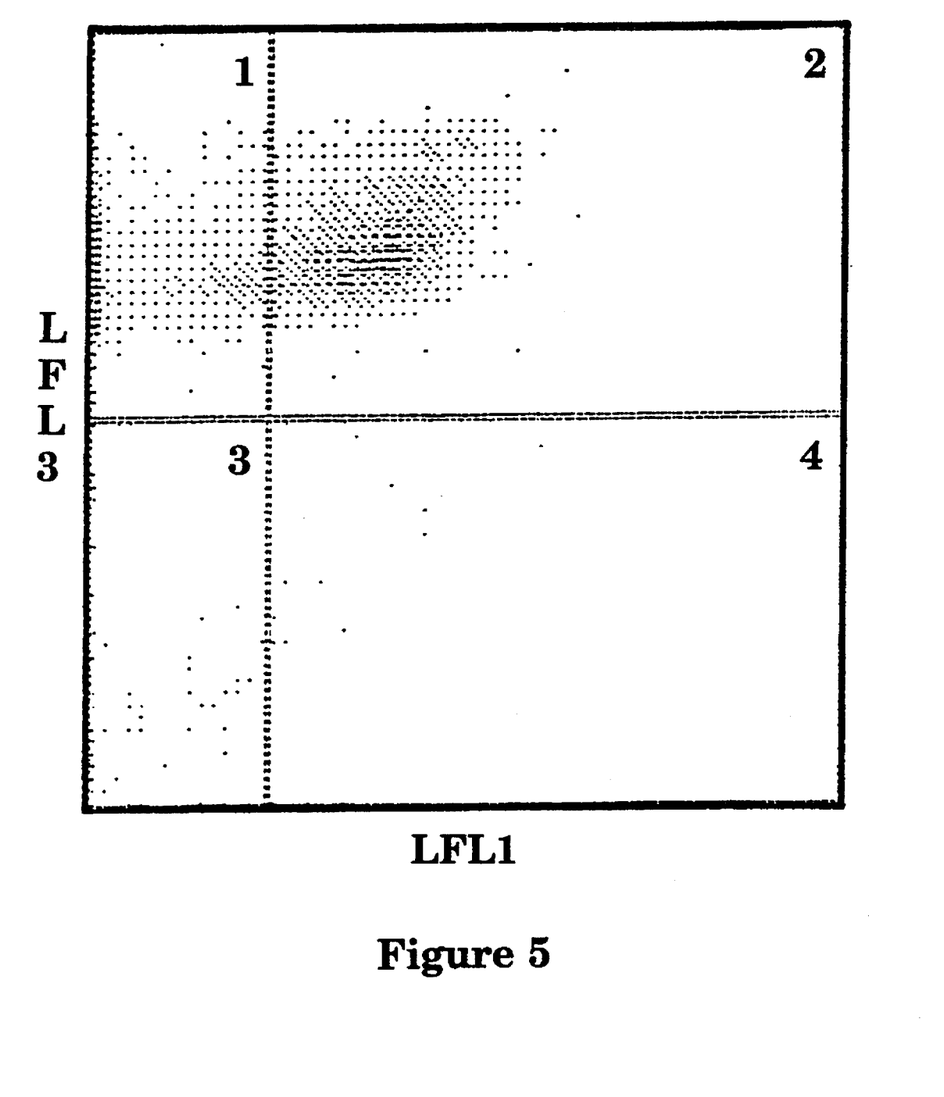
FIG. 5 LFL3 vs. LFL1 plot; HIV-infected cells; with Evans Blue as the background reducing compound (our sample #2065)
Figure 6:
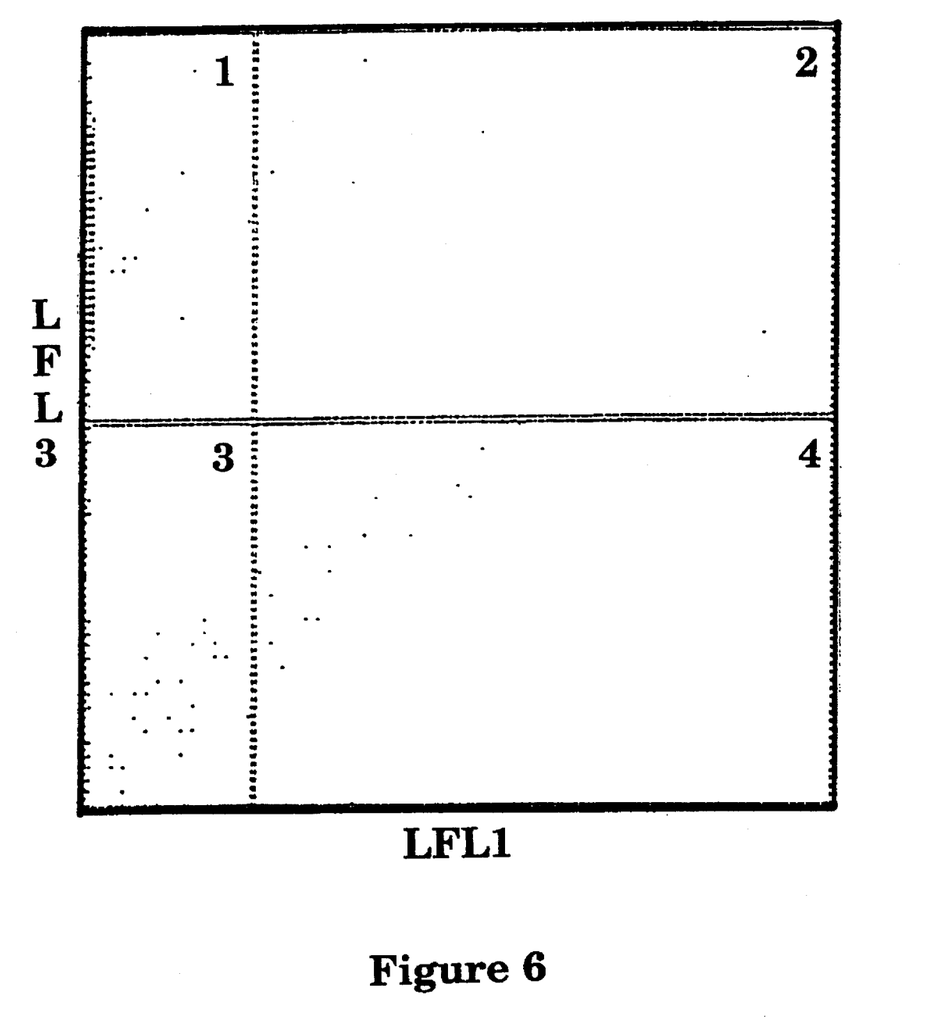
FIG. 6 LFL3 vs. LFL1 plot; uninfected cells; with Evans Blue as the background reducing compound.

The procedures of Example 1 were followed with and without Evans Blue as the background-reducing staining dye. FIG. 3 and FIG. 4 show results obtained without Evans Blue, the difference being that FIG. 3 results were obtained with HIV-infected cells whereas FIG. 4 results were obtained with uninfected cells. FIG. 5 and FIG. 6 show results Evans Blue as the background-reducer, the difference being that FIG. 5 results were obtained with HIV-infected cells whereas FIG. 6 results were obtained with uninfected cells.

The results show that for uninfected cells in the absence of Evans Blue (FIG. 4), 25.4 percent of the cells appeared in quadrant 4. Quadrant 4 is where infected cells will appear when Evans Blue is omitted (See FIG. 3).

The results obtained with Evans Blue were better than those obtained without Evans Blue. For uninfected cells where Evans Blue was used (FIG. 6), only 0.1 percent of the cells appeared in quadrant 2. Quadrant 2 is where infected cells will appear when Evans Blue is used (see FIG. 5).

EXAMPLE 3

Use of Background Reducers with Fluorescent-Labeled Antibody Probe

Aliquots of human white blood cells (WBC) were incubated either in PBS (control cells) or PBS containing a phycoerythrin-labeled Coulter T-8 antibody. Incubations were for 30 min at 22° C. Cells were then washed 3 times in PBS, and resuspended in one of three solutions for flow cytometry (done with a 525 bp filter for FL1): either PBS, a PBS solution containing Naphthol Blue Black, or PBS containing Palatine Fast Black WAN. The results are shown in Table 5.

TABLE 5

| Flow cytometry solution | Antibody-treated cells | control cells |
| --- | --- | --- |
| PBS | 3.729 | .752 |
| PBS + Naphthol Bl. Bl. | 2.915 | .429 |
| PBS + Palatine F-B WAN | 3.131 | .465 |

The results in Table 5 indicate that the presence of Naphthol Blue Black resulted in a 22 percent decrease in signal in the antibody-treated cells and a 43 percent decrease in the control cells. In the presence of Palatine Fast-Black WAN there was a 16 percent decrease in the signal obtained with the antibody-treated cells and a 38 percent decrease in the signal obtained with the control cells.

It can be seen that both Naphthol Blue Black and Palatine Fast Black WAN lead to the desired result: a relatively greater decrease in signal for cells untreated with the probe than in signal for antibody-treated cells.

The relative reductions in background were not as dramatic as those observed in Examples. The difference in the results is most likely due to the fact that a phycoerythrin dye was used in this Example whereas a fluorescein dye was used in Example 1. That could be a result of the fact that fluorescein gives a higher background due to non-specific background than phycoerythrin and therefore the impact of a background reducing compound is greater. Additionally, or alternatively, the differences could be a function of the PMT settings used in the two Examples.

Having thus described the invention, what is desired to protect by Letters Patent and hereby claim is:

1. A process of measuring the amount of target molecules in a biological entity with the aid of a flow cytometer, which process comprises the steps of:

(1) incubating a biological entity with a fluorescent probe in a first solution;

(2) removing the biological entity from that first solution;

(3) suspending the biological entity in a second solution;

(4) exposing the biological entity to light at absorption wavelengths of the fluorescent probe while said biological entity is in said second solution and said second solution is in a flow cytometer, and (5) measuring the amount of light emitted at emission wavelengths of the fluorescent probe while said biological entity is in said second solution and said second solution is in a flow cytometer;

wherein during steps (4) and (5), and optionally during step (3), a background-reducing compound is present in said second solution
wherein a background reducing compound may also be present in the first solution;

wherein said biological entity is a cell or a virus; and
   wherein said background-reducing compound (a) comprises a light-absorbing moiety with a structure different than that of the fluorescent dye moiety of the fluorescent probe;

(b) has an absorption wavelength range that includes the emission wavelengths of the fluorescent probe at which the amount of light is measured in step (5) and (c) has an emission spectrum that differs from that of the fluorescent dye moiety, such that in step (5), due to the presence of the background reducing compound, the amount of background light is reduced, provided it is reduced to an extent greater than the extent to which the amount of light emitted by specifically bound probe molecules is reduced due to the presence of said compound.

2. A process of claim 1 wherein the fluorescent probe comprises an antibody moiety or a nucleic acid moiety.

3. A process of claim 1 which further comprises, between the steps numbered (2) and (3) in claim 1, a step wherein the cell is washed in a probe-free solution.

4. A process of claim 1 wherein the probe comprises a single-stranded nucleic acid moiety.

5. A process of claim 1 wherein the nucleic acid moiety of the probe is single-stranded DNA.

6. A process of claim 1 wherein the probe comprises a nucleic acid moiety specific for a cellular gene of interest or an RNA transcript of such a gene.

7. A process of claim 1 wherein the background-reducing compound is a fluorescent compound.

8. A process of claim 1 wherein the background-reducing compound comprises an azo dye derivative that has a polyaromatic conjugate moiety and, on a that moiety, one or more polar groups.

9. A process of claim 1 wherein the biological entity is a cell.

10. A process of claim 9 where the cell is a eukaryotic cell.

11. A process of claim 10 where the eukaryotic cell is a human cell.

12. A process of claim 11 wherein the probe is specific for viral nucleic acid.

13. A process of claim 12 wherein the viral nucleic acid is human immunodeficiency virus nucleic acid.

14. A process of claim 9 where the cell is a prokaryotic cell.

15. A process of claim 9 wherein the cell is a plant cell.

16. A process of claim 1 wherein the biological entity is a virus.

17. A process of claim 9 wherein the target cell is present as a single cell within a population of cells not as part of a tissue section.

18. A process of claim 1 where the probe comprises an antibody moiety.

19. A process of claim 1 wherein the fluorescent probe dye comprises a fluorescein moiety.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: N ( x i ) SEQUENCE DESCRIPTION: SEQ ID NO:1:

TACGCTCGAT CCAGCTATCA GCCGT 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: N ( x i ) SEQUENCE DESCRIPTION: SEQ ID NO:2:

ATCAGAGTAG TGGTATTTCA CCGGC 25